United States Patent [19]
Shiraishi et al.

[11] 4,058,547
[45] Nov. 15, 1977

[54] CATALYTIC PROCESS FOR THE PRODUCTION OF ACRYLONITRILE

[75] Inventors: Tatsuo Shiraishi; Shinkichi Shimizu; Hiroshi Ichihashi, all of Niihama, Japan

[73] Assignee: Sumitomo Chemical Company, Limited, Japan

[21] Appl. No.: 302,882

[22] Filed: Nov. 1, 1972

Related U.S. Application Data

[62] Division of Ser. No. 148,165, May 28, 1971, Pat. No. 3,746,656.

[30] Foreign Application Priority Data

May 29, 1970 Japan .................................. 45-46667

[51] Int. Cl.² .......................................... C07C 120/14
[52] U.S. Cl. ................................................ 260/465.3
[58] Field of Search ....................................... 260/465.3

[56] References Cited
U.S. PATENT DOCUMENTS

| 3,226,422 | 12/1965 | Sennewald et al. | 260/465.3 |
| 3,254,110 | 5/1966 | Sennewald et al. | 260/465.3 |
| 3,312,710 | 4/1967 | Sakuyama et al. | 260/465 C X |
| 3,338,952 | 8/1967 | Callahan et al. | 260/465.3 |
| 3,452,077 | 6/1969 | Caporali et al. | 260/465 C |
| 3,478,082 | 11/1969 | Huibers | 260/465.3 |
| 3,479,385 | 11/1969 | Huibers | 260/465 C |
| 3,625,867 | 12/1971 | Yoshino et al. | 260/465.3 X |
| 3,642,930 | 2/1972 | Grasselli et al. | 260/465.3 X |

FOREIGN PATENT DOCUMENTS 45-35287   11/1970   Japan .................................. 260/465.3

Primary Examiner—Joseph Paul Brust
Attorney, Agent, or Firm—Craig & Antonelli

[57] ABSTRACT

In the production of acrylonitrile by a vapor phase reaction of propylene, ammonia and oxygen at an elevated temperature, a process which comprises contacting propylene, ammonia and oxygen with a catalyst composition comprising a catalyst system of the formula: $Tl_a P_b Mo_c Fe_d Bi_e X_f O_g$ wherein X represents one or more of the metals, Ni, Mg and Co, and $a, b, c, d, e, f$ and $g$ represent respectively the relative number of atoms of each component; provided that when $c$ is 12, $a$ is 2 or less, but not 0; $b$ is 0 to 5; $d$ is 0.1 to 5; $e$ is 0.1 to 5; $f$ is 2 to 15; and the value of $g$ depends on the number of the other atoms and is usually from 38.3 to 81.5.

29 Claims, No Drawings

CATALYTIC PROCESS FOR THE PRODUCTION OF ACRYLONITRILE

This is a division of application Ser. No. 148,165 filed May 28, 1971, now U.S. Pat. No. 3,746,656.

The present invention relates to a process for producing acrylonitrile. More particularly, the invention relates to a process for selective production of acrylonitrile by the vapor phase reaction of propylene, ammonia and oxygen in the presence of a specific catalyst system.

For the production of acrylonitrile by ammoxidation of propylene, there have been proposed a variety of catalyst systems, some examples of these systems are as follows: a catalyst system comprising bismuth, tin or antimony salt of molybdic acid or phosphomolybdic acid, or bismuth phosphowolframate (Japanese patent publication No. 5870/1961); a catalyst system comprising the oxides of molybdenum, phosphorus, bismuth and iron (Japanese patent publication No. 17967/1963); a catalyst system comprising the oxides of copper and antimony (Japanese patent publicationNo. 14093/1966); a catalyst system comprising the oxides of bismuth and tungsten (Japanese patent publication No. 27402/1968); a catalyst system comprising the oxides of uranium and antimony (Japanese patent publication No. 24367/1965), etc. However, some drawbacks are seen in these known catalyst systems.

One of the drawbacks is the production of acrylonitrile in a relatively low selectivity. Thus, there are by-produced carbon monoxide, carbon dioxide, acrolein, acetaldehyde, acetonitrile, hydrogen cyanide and the like, in large amounts, which reduce the yield of acrylonitrile. Moreover, the production of such by-products results not only in the loss of the starting materials, but also in the difficult recovery of the desired acrylonitrile.

Another drawback is the low yield of acrylonitrile in each pass of propylene feed. This is probably due to the low conversion of propylene or, even if the conversion of propylene may be high, the low selectivity to acrylonitrile.

A further drawback of these known systems is the production of excessively oxidized by-products such as carbon monoxide and carbon dioxide, which makes the control of heat difficult. The side reactions are more exothermic than the main reaction, and a larger amount of a diluent is required to control the heat generating therefrom.

As a result of extensive studies, it has been found in accordance with this invention that the use of a specific catalyst system comprising thallium in the ammoxidation of propylene will afford acrylonitrile with a high selectivity in an excellent yield per each pass. It has also been found that this use of this system suppresses considerably the formation of undesirable by-products, especially carbon monixide and carbon dioxide, and makes it possible to carry out the reaction at a relatively low temperature. The present invention is based on these findings.

According to the present invention, the vapor phase reaction of propylene, ammonia and oxygen is carried out in the presence of a catalyst system corresponding to the formula: $Tl_aP_bMo_cFe_dBi_eX_fO_g$ wherein X represents one or more metals selected from the group consisting of Ni, Mg and Co, and $a$, $b$, $c$, $d$, $e$, $f$ and $g$ represent, respectively, the number of atoms of each component; provided that when $c$ is 12, $a$ is 2 or less (preferably 0.01 to 1.0), but not 0; $b$ is 0 to 5 (preferably 0.01 to 3.0); $d$ is 0.1 to 5; $e$ is 0.1 to 5 (preferably 0.5 to 3.0); $f$ is 2 to 15 (preferably 2 to 12); and $g$ is decided or determined depending on the number of the other atoms and is usually from 38.3 to 81.5 (preferably 38.9 to 69.0).

The starting materials in the ammoxidation of this invention are propylene, ammonia and oxygen. The propylene is not necessarily required to be highly pure and may contain, for instance, some amounts of low molecular weight saturated hydrocarbons such as propane. As the oxygen source, there may be used pure oxygen gas, air enhanced or not in the oxygen concentration or any other free oxygen-containing gas. From the economical viewpoint, the use of air is preferred. In order to increase the selectivity to acrylonitrile, steam may be introduced into the reaction system, but this introduction is not necessarily required. If desired, an appropriate inert gas such as nitrogen, carbon dioxide, or argon, may be used as a diluent.

For preparation of the catalyst system, there may be employed metallic thallium and thallium compounds (e.g. thallium nitrate, thallium carbonate, and thallium chloride), molybdenum compounds (e.g., ammonium molybdate, molybdenum oxide, molybdic acid and phosphomolybdic acid), phosphorus compounds (e.g., phosphoric acid, ammonium phosphate, and phosphorus pentoxide), iron compounds (e.g., ferric nitrate, and ferric chloride), bismuth compounds (e.g., bismuth nitrate, bismuth chloride and bismuth oxide), magnesium compounds (e.g., magnesium nitrate, and magnesium chloride), cobalt compounds (e.g., cobalt nitrate, and cobalt chloride) and nickel compounds (e.g., nickel nitrate and nickel chloride).

The catalyst system may be used as such but it is advantageously incorporated with a suitable carrier (e.g., silica, alumina, silicon carbide, titanium oxide). The amount of the carrier is varied with its kind and may be usually less than 90% by weight, preferably from 5 to 90% by weight, of the catalyst composition. The catalyst composition is normally formed in tablets or granules on use.

The preparation of the mixed oxide catalyst composition of this invention may be executed by a per se conventional procedure. For instance, a thallium salt, an iron salt, a bismuth salt, a phosphorus compound and one or more of a magnesium salt, a cobalt salt and a nickel salt are added to an aqueous solution of a molybdate such as ammonium molybdate; the resulting slurry is admixed with a carrier material and evaporated to dryness; and the resultant cake is calcined at an elevated temperature in atmosphere and, after cooling, crushed and shaped into pellets or granules.

The production of acrylonitrile using the catalyst composition of the invention may be effected by a fluidized bed processor a fixed bed process. The reaction temperature is associated with the kind of the catalyst composition and usually is from about 300° to about 520° C, preferably from about 350° to about 480° C. The reaction is usually carried out at a nearly atmospheric pressure (preferably about 0.7 to about 5 atm). The molar ratio of the starting materials may be propylene: ammonia: oxygen = 1.0 : 0.7-2.5 (favorably 1.0-2.0): 1.0-5.0 (favorably 1.5-3.5). When steam is used, it may be usually not more than about 18 mol, favorably from about 1 to about 10 mol per 1 mol of propylene. The space velocity of the reactants is ordinarily from about 50 to about 2000 hr$^{-1}$, preferably from about 100 to about 1000 hr$^{-1}$.

By the use of the catalyst system of the present invention, the desired acrylonitrile can be produced in a high selectivity and an excellent yield per each pass with little by-production of carbon monoxide and carbon dioxide. In addition, the life of the catalytic activity is sufficiently and satisfactorily long and the thallium in the catalyst composition is never volatilized during the reaction.

A number of preferred embodiments of the present invention are shown in the following Examples.

EXAMPLE 1

Nickel nitrate (32.72 g), cobalt nitrate (29.10 g), ferric nitrate (5.05 g) and thallium nitrate (3.33g) are dissolved in distilled water (300 ml) and bismuth nitrate (12.13 g) is dissolvedin dilute nitric acid (6% by weight; 25 ml). These solutions are combined together. The resultant mixture is added to a solution of ammonium molybdate (52.98 g) in dilute aqueous ammonia (3.5% by weight; 300 ml) containing phosphoric acid (85% by weight; 0.23 g). To the resultant slurry dispersion, silica sol ($SiO_2$, 20% by weight; 100 ml) is added, and the mixture is evaporated to dryness until the generation of nitrogen dioxide is ceased. The residue is calcined at 300° C for 3 hours (1st calcination), cooled and crushed. The obtained powder is tableted and calcined at 525° C for 6 hours (2nd calcination) to give a catalyst composition, of which the active components correspond to the formula: $Tl_{0.5} P_{0.08} Mo_{12} Fe_{0.5} Bi_1 Ni_{4.5} Co_4 O_{47.7}$ (wherein the carrier is omitted).

In a glass-made reaction tube of 10 mm in inner diameter, the above obtained catalyst composition (6.3 ml) is charged and heated up to 430° C. Then, a gaseous mixture of propylene, ammonia, oxygen, steam and nitrogen (1.0 : 1.2 : 3.0 : 4.9 : 7.6 in molar ratio) is introduced into the reaction tube at a space velocity of 476 $hr^{-1}$, whereby acrylonitrile is produced.

The conversion of propylene is 91% and the selectivities to acrylonitrile, carbon monoxide and carbon dioxide are respectively, 85.5%, 2.5% and 3.8%, calculated according to the following equations:

$$\text{Conversion of propylene (\%)} = \frac{\text{Reacted propylene (mol)}}{\text{Feed propylene (mol)}} \times 100$$

$$\text{Selectivity (\%)} = \frac{\text{Weight of carbon atoms in product}}{\text{Weight of carbon atoms in reacted propylene}} \times 100$$

EXAMPLE 2

In the same manner as in Example 1, except that magnesium nitrate (25.64g) is used in place of cobalt nitrate and the amounts of ferric nitrate and thallium nitrate are changed, respectively to 8.08 g and 1.33 g, a catalyst composition of which the active components correspond to the formula: $Tl_{0.2} P_{0.08} Mo_{12} Fe_{0.8} Bi_1 Ni_{4.5} Mg_4 O_{47.7}$ is prepared.

As in Example 1, a gaseous mixture of propylene, ammonia, oxygen, steam and nitrogen (1.0 : 1.2 : 3.1 : 4.8 : 7.4 in molar ratio) is contacted with the above obtained catalyst composition (5.8 ml) at 410° C at a space velocity of 580 $hr^{-1}$, whereby acrylonitrile is produced. The conversion of propylene is 99.7% and the selectivities to acrylonitrile, carbon monoxide and carbon dioxide are, respectively, 83.4%, 2.1% and 6.1%.

EXAMPLE 3

In the same manner as in Example 1, except that cobalt nitrate is not used and the amounts of nickel nitrate, ferric nitrate and thallium nitrate are changed, respectively, to 61.80 g, 8.08 g and 1.33 g, a catalyst composition of which the active components correspond to the formula: $Tl_{0.2} P_{0.08} Mo_{12} Fe_{0.8} Bi_1 Ni_{8.5} O_{47.7}$ is prepared.

As in Example 1, a gaseous mixture of propylene, ammonia, oxygen, steam and nitrogen (1.0 : 1.1 : 2.9 : 3.8 : 6.8 in molar ratio) is contacted with the above-obtained catalyst composition (6.1 ml) at 430° C at a space velocity of 620$hr^{-1}$, whereby acrylonitrile is produced. The conversion of propylene is 100% and the selectivities to acrylonitrile, carbon monoxide and carbon dioxide are, respectively, 80%, 5.0% and 6.2%.

EXAMPLE 4

In the same manner as in Example 1, except that magnesium nitrate (54.49 g) is used in place of nickel nitrate, cobalt nitrate is not used, and the amounts of ferric nitrate and thallium nitrate are changed, respectively to 10.10 g and 1.33 g, a catalyst composition of which the active components correspond to the formula: $Tl_{0.2} P_{0.08} Mo_{12} Fe_1 Bi_1 Mg_{8.5} O_{48.0}$ is prepared.

As in Example 1, a gaseous mixture of propylene, ammonia, oxygen, steam and nitrogen (1.0 : 1.1 : 2.9 : 3.8 : 6.8 in molar ratio) is contacted with the above-obtained catalyst composition (6.1 ml) at 430° C at a space velocity of 394 $hr^{-1}$, whereby acrylonitrile is produced. The conversion of propylene is 90% and the selectivities to acrylonitrile, carbon monoxide, and carbon dioxide are, respectively, 78%, 4.6% and 4.3 %.

EXAMPLE 5

In the same manner as in Example 1, except that nickel nitrate is not used, the amounts of cobalt nitrate, ferric nitrate, and thallium nitrate are changed, respectively, to 61.84 g, 10.10 g and 1.33 g and the calcination after molding is executed at 550° C, a catalyst composition of which the active components correspond to the formula: $Tl_{0.2} P_{0.08} Mo_{12} Fe_1 Bi_1 Co_{8.5} O_{48.0}$ is prepared.

As in Example 1, a gaseous mixture of propylene, ammonia, oxygen, steam and nitrogen (1.0 : 1.1 : 3.0 : 4.8 : 7.5 in molar ratio) is contacted with the above-obtained catalyst composition (5.9 ml) at 440° C at a space velocity of 518 $hr^{-1}$, whereby acrylonitrile is produced. The conversion of propylene is 90.5% and the selectivities to acrylonitrile, carbon monoxide and carbon dioxide and respectively 84%, 3.0% and 3.8%.

EXAMPLE 6

In the same manner as in Example 1, except that magnesium nitrate (25.64 g) is used in place of cobalt nitrate, and phosphoric acid (85% by weight; 0.86 g) is added, a catalyst composition of which the active components correspond to the formula: $Tl_{0.5} P_{0.3} Mo_{12} Fe_{0.5} Bi_1 Ni_{4.5} Mg_4 O_{48.25}$ is prepared.

As in Example 1, a gaseous mixture of propylene, ammonia, oxygen, steam and nitrogen (1.0 : 1.7 : 3.0 : 7.5 : 6.5 in molar ratio) is contacted with the above-obtained catalyst (6.2 ml) at 410° C at a space velocity of 560 $hr^{-1}$, whereby acrylonitrile is produced. The conversion of propylene is 90% and the selectivities to acrylonitrile, carbon monoxide, and carbon dioxide are, respectively 86%, 1.7% and 4.0%.

REFERENCE EXAMPLE

In the same manner as in Example 3, except that thallium nitrate is not used, a catalyst composition of which the active components correspond to the formula: $P_{0.08}Mo_{12}Fe_{0.8}Bi_1Ni_{8.5}O_{50.4}$ is prepared.

As in Example 1, a gaseous mixture of propylene, ammonia, oxygen, steam and nigrogen (1.0 : 1.2 : 3.0 : 3.8 : 7.0 in molar ratio) is contacted with the above-obtained catalyst composition (8.0 ml) at 390° C at a space velocity of 435 hr$^{-1}$, whereby acrylonitrile is produced. The conversion of propylene is 90%, and the selectivities to acrylonitrile, carbon monoxide and carbon dioxide are respectively 51%, 11% and 16%.

What is claimed is:

1. A process for producing acrylonitrile by the vapor phase reaction of propylene, ammonia and gaseous oxygen at a temperature from about 300° to about 520° C., which comprises contacting propylene, ammonia and gaseous oxygen with a catalyst composition comprising a catalyst system of the formula: $Tl_aP_bMo_cFe_dBi_eX_fO_g$ wherein X is Ni, Mg or Co or mixtures thereof and $a$, $b$, $c$, $d$, $e$, $f$ and $g$ represent respectively, the number of atoms and $c$ is 12, $a$ is 2 or less, but not 0; $b$ is 0 to 5; $d$ is 0.1 to 5; $e$ is 0.1 to 5; $f$ is 2 to 15; and $g$ is from 38.3 to 81.5.

2. The process according to claim 1, wherein the molar ratio of the starting materials is propylene : ammonia : oxygen = 1.0 : 0.7–2.5 : 1.0–5.0.

3. The process according to claim 1, wherein the molar ratio of the starting materials is propylene : ammonia : oxygen = 1.0 : 1.0–2.0 : 1.5–3.5.

4. The process according to claim 1, wherein the reaction is effected in the presence of steam.

5. The process according to claim 1, wherein the steam is employed in a rate of not more than about 18 mol per 1 mol of propylene.

6. The process according to claim 1, wherein the steam is employed in a rate of about 1 to about 10 mol per 1 mol of propylene.

7. The process according to claim 1, wherein the reaction is effected at a temperature from about 350° to about 480° C.

8. The process according to claim 1, wherein the space velocity is from about 50 to about 2000 hr$^{-1}$.

9. The process according to claim 1, wherein the space velocity is from about 100 to about 1000 hr$^{-1}$.

10. The process according to claim 1, wherein the reaction is effected at a pressure of from about 0.7 to about 5 atmospheres.

11. The process according to claim 1, wherein air enhanced or not in the oxygen concentration is employed as the oxygen source.

12. The process according to claim 1, wherein the reaction is effected in the presence of a diluent selected from the group consisting of nitrogen, carbon dioxide and argon.

13. A process according to claim 1, wherein the catalyst composition consists essentially of said catalyst system.

14. A process according to claim 1, wherein the catalyst composition consists of said catalyst system.

15. A process according to claim 1, wherein said catalyst composition is incorporated with a carrier selected from the group consisting of silica, alumina, silicon carbide and titanium oxide.

16. A process according to claim 15, wherein the amount of the carrier is from 5 to 90% by weight of said catalyst composition.

17. A process according to claim 1, wherein $a$ is at least about 0.01.

18. A process according to claim 1, wherein $a$ is about 0.01 to 1.0.

19. A process according to claim 1, wherein $a$ is 0.01 to 1.0, $b$ is 0.01 to 3.0, $c$ is 12, $d$ is 0.1 to 5, $e$ is 0.5 to 3.0, $f$ is 2 to 12, and $g$ is from 38.9 to 69.0.

20. A process according to claim 1, wherein $a$ is about 0.2 to 0.5.

21. A process according to claim 1, wherein X is Ni and further wherein $a$ is at least about 0.01.

22. A process for producing acrylonitrile by the vapor phase reaction of propylene, ammonia and gaseous oxygen at a temperature of about 300° to about 520° C, which comprises contacting propylene, ammonia and gaseous oxygen with a catalyst composition consisting essentially of a catalyst system of formula: $Tl_aP_bMo_cFe_dBi_eX_fO_g$ wherein X is Ni, Mg or Co or mixtures thereof and $a$, $b$, $c$, $d$, $e$, $f$ and $g$ represent respectively, the number of atoms and $c$ is 12, $a$ is 2 or less, but not 0; $b$ is 0 to 5; $d$ is 0.1 to 5; $e$ is 0.1 to 5; $f$ is 2 to 15 and $g$ is from 38.3 to 81.5, said catalyst formed by admixing a slurry of an aqueous solution of a molybdate with a thallium salt, an iron salt, a bismuth salt, a phosphorous compound and one or more of a magnesium salt, a cobalt salt and a nickel salt with a carrier material, evaporating the composition so formed to dryness to form a cake, calcining the cake at an elevated temperature and cooling the calcined cake.

23. A process according to claim 22, wherein X is Ni, and wherein $a$ is at least about 0.01.

24. A process according to claim 1, wherein the catalyst composition consists essentially of said catalyst system and a carrier.

25. A process according to claim 24, wherein said catalyst composition consists of said catalyst system and said carrier selected from the group consisting of silica, alumina, silicon carbide and titanium oxide.

26. A process according to claim 22, wherein said thallium salt, said iron salt, said bismuth salt, said magnesium salt, said cobalt salt, and said nickel salt are nitrates, wherein said molybdate is ammonium molybdate, and wherein said phosphorous compound is phosphoric acid.

27. A process according to claim 22, wherein $a$ is at least about 0.01.

28. A process according to claim 22, wherein $a$ is about 0.01 to 1.0.

29. A process according to claim 22, wherein $a$ is 0.01 to 1.0, $b$ is 0.01 to 3.0, $c$ is 12, $d$ is 0.1 to 5, $e$ is 0.5 to 3.0, $f$ is 2 to 12 and $g$ is from 38.9 to 69.0.

* * * * *